United States Patent
Lai et al.

(10) Patent No.: US 8,021,643 B2
(45) Date of Patent: *Sep. 20, 2011

(54) MCM-22 FAMILY MOLECULAR SIEVE COMPOSITION

(75) Inventors: Wenyih Frank Lai, Bridgewater, NJ (US); Robert Ellis Kay, Easton, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/912,523

(22) Filed: Oct. 26, 2010

(65) Prior Publication Data

US 2011/0038789 A1 Feb. 17, 2011

Related U.S. Application Data

(62) Division of application No. 11/657,192, filed on Jan. 24, 2007, now Pat. No. 7,846,418.

(60) Provisional application No. 60/773,014, filed on Feb. 14, 2006.

(51) Int. Cl.
*C01B 39/46* (2006.01)

(52) U.S. Cl. .................. 423/718; 423/702; 423/706

(58) Field of Classification Search .......... 423/702, 423/706, 718; 208/46, 111.01, 135
See application file for complete search history.

(56) References Cited

U.S. PATENT DOCUMENTS

| | | |
|---|---|---|
| 4,439,409 A | 3/1984 | Puppe et al. |
| 4,826,667 A | 5/1989 | Zones et al. |
| 4,954,325 A | 9/1990 | Rubin et al. |
| 4,954,663 A | 9/1990 | Marler et al. |
| 4,956,514 A | 9/1990 | Chu |
| 4,962,239 A | 10/1990 | Bell et al. |
| 4,962,250 A | 10/1990 | Dessau et al. |

(Continued)

FOREIGN PATENT DOCUMENTS

WO   WO 97/17290   5/1997

(Continued)

OTHER PUBLICATIONS

Corma et al., "*Synthesis and Characterization of the MCM-22 Zeolite*", Zeolite vol. 15 (1995), pp. 2-8.

(Continued)

*Primary Examiner* — David M Brunsman
(74) *Attorney, Agent, or Firm* — Darryl M. Tyus; Xiaobing Feng

(57) ABSTRACT

An MCM-22 family molecular sieve having an X-ray diffraction pattern of the as-synthesized MCM-22 family molecular sieve including d-spacing maxima at 12.4±0.25, 3.57±0.07 and 3.42±0.07 Angstroms and at least one peak between 26.6° and 29° (2θ). The peak between 26.6° to 29° (2θ) has a two theta (2θ) of about 26.9°. A method of manufacturing an MCM-22 family molecular sieve, said method comprising the steps of (a) combining at least one silicon source, at least one source of alkali metal hydroxide, at least one directing-agent (R), water, and optionally one aluminum source, to form a mixture having the following mole composition:

$Si:Al_2$=10 to infinity
$H_2O:Si$=1 to 20
$OH^-:Si$=0.001 to 2
$M^+:Si$=0.001 to 2
$R:Si$=0.001 to 0.34 wherein M is an alkali metal; (b) treating said mixture at crystallization conditions for less than 72 hr to form a treated mixture having said MCM-22 family molecular sieve, wherein said crystallization conditions comprises a temperature range from about 160° C. to about 250° C.; and (c) recovering said MCM-22 family molecular sieve.

25 Claims, 2 Drawing Sheets

U.S. PATENT DOCUMENTS

| | | | |
|---|---|---|---|
| 4,962,256 A | 10/1990 | Le et al. | |
| 4,962,257 A | 10/1990 | Absil et al. | |
| 4,973,781 A | 11/1990 | Valyocsik et al. | |
| 4,973,784 A | 11/1990 | Han et al. | |
| 4,982,033 A | 1/1991 | Chu et al. | |
| 4,982,040 A | 1/1991 | Angevine et al. | |
| 4,983,276 A | 1/1991 | Absil et al. | |
| 4,986,894 A | 1/1991 | Keville et al. | |
| 4,992,606 A | 2/1991 | Kushnerick et al. | |
| 4,992,611 A | 2/1991 | Morrison | |
| 4,992,615 A | 2/1991 | Huss, Jr. et al. | |
| 5,000,839 A | 3/1991 | Kirker et al. | |
| 5,001,283 A | 3/1991 | Altman et al. | |
| 5,001,295 A | 3/1991 | Angevine et al. | |
| 5,001,296 A | 3/1991 | Howley et al. | |
| 5,012,033 A | 4/1991 | Child et al. | |
| 5,019,664 A | 5/1991 | Del Rossi et al. | |
| 5,019,665 A | 5/1991 | Partridge et al. | |
| 5,019,670 A | 5/1991 | Le et al. | |
| 5,236,575 A | 8/1993 | Bennett et al. | |
| 5,250,277 A | 10/1993 | Kresge et al. | |
| 5,362,697 A | 11/1994 | Fung et al. | |
| 6,077,498 A | 6/2000 | Diaz Cabanas et al. | |
| 6,936,744 B1 | 8/2005 | Cheng et al. | |
| 7,799,316 B2 * | 9/2010 | Lai et al. | 423/706 |
| 7,816,573 B2 * | 10/2010 | Lai et al. | 585/467 |
| 7,829,062 B2 * | 11/2010 | Lai et al. | 423/700 |
| 7,842,277 B2 * | 11/2010 | Roth et al. | 423/718 |
| 7,846,418 B2 * | 12/2010 | Lai et al. | 423/718 |

FOREIGN PATENT DOCUMENTS

| | | |
|---|---|---|
| WO | WO 2005/118476 | 12/2005 |
| WO | WO 2006/015824 | 2/2006 |
| WO | WO 2006/015825 | 2/2006 |
| WO | WO 2006/015826 | 2/2006 |

OTHER PUBLICATIONS

Guray et al., "*Synthesis of Zeolite MCM-22 Under Rotating and Static Conditions*", Microporous and Mesoporous Materials vol. 31, 1999, pp. 241-251.

Marques et al., "*Static Crystallization of Zeolites MCM-22 and MCM-49*", Microporous and Mesoporous Materials, vol. 32 (1999), pp. 131-145.

Mochida et al., "*The Effects of Seeding in the Synthesis of Zeolite MCM-22 in the Presence of Hexamethyleneimine*", Zeolites (1997), vol. 18, pp. 142-151.

Ravishankar et al., "*Characterization and Catalytic Properties of Zeolite MCM 22*", Microporous Materials vol. 4 (1995), pp. 83-93.

\* cited by examiner

XRD of As-synthesized Products of Examples 1 & 2

XRD of Calcined Products of Examples 1 & 2

SEM of Example 1

SEM of Example 2

MCM-22 FAMILY MOLECULAR SIEVE COMPOSITION

PRIORITY CLAIM

This application is a divisional of and claims priority to U.S. patent application Ser. No. 11/657,192, filed Jan. 24, 2007, now U.S. Pat. No. 7,846,418, and U.S. Provisional Application No. 60/773,014, filed Feb. 14, 2006, the disclosure of which is herein incorporated by reference in their entireties.

FIELD

This invention relates to a novel MCM-22 family molecular sieve composition and the use of the same for hydrocarbon conversions.

BACKGROUND OF THIS INVENTION

Molecular sieve materials, both natural and synthetic, have been demonstrated in the past to have catalytic properties for various types of hydrocarbon conversion. Certain molecular sieves, zeolites, AlPOs, mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Since the dimensions of these pores are such as to accept for adsorption molecules of certain dimensions while rejecting those of larger dimensions, these materials have come to be known as "molecular sieve" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table (IUPAC 1997) Group IIIA element oxide (e.g., $AlO_4$). The tetrahedra are cross-linked by the sharing of oxygen atoms whereby the ratio of the total Group IIIA element (e.g., aluminum) and silicon atoms to oxygen atoms is 1:2. The electrovalence of the tetrahedra containing the Group IIIA element (e.g., aluminum) is balanced by the inclusion in the crystal of a cation, for example a proton, an alkali metal or an alkaline earth metal cation. This can be expressed wherein the ratio of the Group IIIA element (e.g., aluminum) to the number of various cations, such as $H^+$, $Ca^{2+}/2$, $Sr^{2+}/2$, $Na^+$, $K^-$, or $Li^+$, is equal to unity.

Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a hydrothermal reaction mixture containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a hydrothermal reaction mixture containing an adamantane quaternary ammonium ion. U.S. Pat. No. 6,077,498 refers to a crystalline molecular sieve composition of matter named ITQ-1 and its synthesis from a hydrothermal reaction mixture containing one or a plurality of organic additives.

The term "MCM-22 family material" (or "material of the MCM-22 family" or "molecular sieve of the MCM-22 family"), as used herein, includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1

(described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom.

It is known that crystal morphology can affect catalyst behavior, especially with regard to catalyst activity and stability. It is generally desired to have an MCM-22 material having higher crystallinity and/or thicker platelet morphology likewise favor higher stability.

SUMMARY OF THIS INVENTION

In one embodiment, this invention relates to an MCM-22 family molecular sieve having an X-ray diffraction pattern of the as-synthesized MCM-22 family molecular sieve including d-spacing maxima at 12.4±0.25, 3.57±0.07 and 3.42±0.07 Angstroms and at least one peak between 26.6° and 29° (2θ), using copper K-alpha radiation.

In another embodiment, this invention relates to an MCM-22 family molecular sieve having an X-ray diffraction pattern of the as-synthesized MCM-22 family molecular sieve including values substantially as Table I and a peak between 26.6° to 29° (2θ).

In yet another embodiment, this invention relates to an MCM-22 family molecular sieve which has a platelet morphology having a thickness at least 300 Å measured by SEM.

In another embodiment, this invention relates to an MCM-22 family molecular sieve having an external surface area less than 110 m$^2$/g measured by BET.

In an embodiment, this invention relates to an MCM-22 family molecular sieve having a mesitylene uptake of less than 29 mg/g measured at 0.266 kPa-a (2 torr) mesitylene partial pressure and 100° C.

In another embodiment, the MCM-22 family molecular sieve of this invention is characterized by any combination of the abovementioned features.

In another embodiment, this invention also relates to a method of manufacturing an MCM-22 family molecular sieve of any one of the preceding paragraphs, the method comprising the steps of:
(a) combining at least one silicon source, at least one source of alkali metal hydroxide, at least one directing-agent (R), water, and optionally one aluminum source, to form a mixture having the following mole composition:
Si:Al$_2$=10 to infinity
H$_2$O:Si=1 to 20
OH$^-$:Si=0.001 to 2
M$^+$:Si=0.001 to 2
R:Si=0.001 to 0.34
wherein M is an alkali metal;
(b) treating the mixture at crystallization conditions for less than 72 hr to form a treated mixture having the MCM-22 family molecular sieve, wherein the crystallization conditions comprises a temperature range from about 160° C. to about 250° C.; and
(c) recovering the molecular sieve.

In an embodiment, this invention relates to a process for hydrocarbon conversion, the process comprising the steps of:
(a) contacting a hydrocarbon feedstock with an MCM-22 family molecular sieve recited in any one of the preceding paragraphs under conversion conditions to form a product; and
(b) withdrawing the product.

These and other facets of the present invention shall become apparent from the following detailed description, figure, and appended claims.

DETAILED DESCRIPTION OF THIS INVENTION

Introduction

Figure 1:
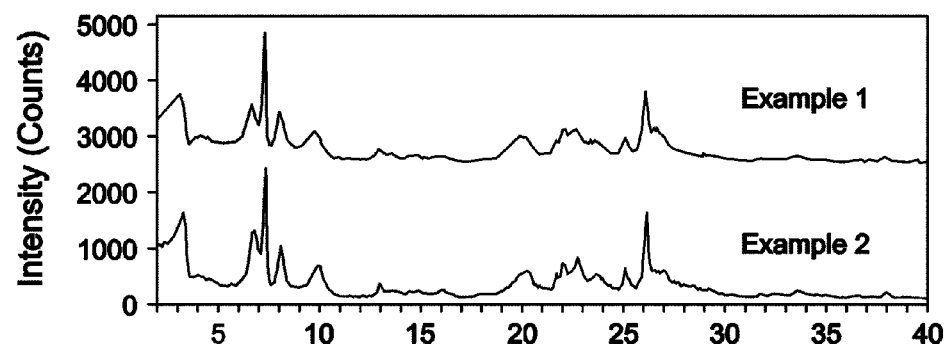
FIG. 1 shows X-ray diffraction patterns of the as-synthesized MCM-22 family molecular sieve products of Examples 1 and 2.

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). The MCM-22 family materials of this invention have preferably substantially free of non-MCM-22 family material(s). The term "substantially free of non-MCM-22 family material(s)" used herein means the MCM-22 family material of this invention preferably contains the minor proportion (less than 50 wt. %), preferably less than 20 wt. %, more preferably less than 10 wt. %, even more preferably less than 5 wt. %, and most preferably less than 1 wt. %, of such impurities in the MCM-22 family materials, which weight percent (wt. %) values are based on the combined weight of impurities and pure phase MCM-22 family materials.

It is to be understood that throughout this detailed description, common characterization techniques were used to describe zeolite materials. These common techniques included ascertaining:

(a) structure and the degree of crystallinity of the molecular sieve material by XRD;
(b) morphology and crystal size of the molecular sieve material measured by Scanning Electron Microscope (SEM);
(c) chemical composition by atomic absorption spectrometry and/or Inductively Coupled Plasma Mass Spectrometry (ICP-MS or ICPMS);
(d) chemical environment of the elements, e.g., Si, Al, and P, in the molecular sieve material using the technique of solid-state MAS (magic angle sample spinning)-NMR of $^{29}$Si, $^{27}$Al, and $^{31}$P;
(e) external hydroxide densities measured by $^1$H solid-state magic angle spinning (MAS) nuclear magnetic resonance (NMR);
(f) adsorption capacities and surface areas measured by Brunauer-Emmett-Teller (BET) method;
(g) surface acidities measured by chemisorption or TGA; and
(h) catalytic activities and catalytic stabilities measured by probing reactions.

X-Ray Powder Diffraction Pattern of Known MCM-22

The known MCM-22 crystalline material has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, the material has a formula, on an anhydrous basis and in terms of moles of oxides per n moles of $YO_2$, as follows:

$$(0.005\text{-}0.1)M_2O:(1\text{-}4)R:X_2O_3:nYO_2$$

wherein M is an alkali or alkaline earth metal, and R is an organic moiety. The M and R components are associated with the material as a result of their presence during synthesis, and are easily removed by post-synthesis methods hereinafter more particularly described.

The known MCM-22 crystalline materials may be distinguished from other crystalline materials by the X-ray diffraction pattern.

The X-ray diffraction data defining in this invention were collected with a Scintag diffraction system, equipped with a germanium solid state detector, using copper K-alpha radiation. The diffraction data were recorded by step-scanning at 0.02 degrees of two-theta (2θ), where theta (θ) is the Bragg angle, and a counting time of 10 seconds for each step. The interplanar spacings, d's, were calculated in Å units (Å), and the relative intensities of the lines, $I/I_o$, one-hundredth of the intensity of the strongest line, above background, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0 to 20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

It should be understood that this X-ray diffraction pattern is characteristic of all the species of the present crystalline composition. The sodium form as well as other cationic forms reveal substantially the same pattern with some minor shifts in interplanar spacing and variation in relative intensity. Other minor variations can occur, depending on the Y to X, e.g., silicon to aluminum, ratio of the particular sample, as well as its degree of thermal treatment (e.g., calcination).

In its as-synthesized form, the known MCM-22 crystalline material has an X-ray diffraction pattern which is distinguished from the patterns of other known crystalline materials by the lines listed in Table I below:

TABLE I

| Interplanar d-Spacing (Å) | Relative Intensity, $I/I_o \times 100$ |
|---|---|
| 13.53 ± 0.2 | M-VS |
| 12.38 ± 0.2 | M-VS |
| 11.13 ± 0.2 | W-S |
| 9.15 ± 0.15 | W-S |
| 6.89 ± 0.15 | W-M |
| 4.47 ± 0.1 | W-M |
| 3.95 ± 0.08 | W-VS |
| 3.56 ± 0.06 | W-M |
| 3.43 ± 0.06 | M-VS |
| 3.36 ± 0.05 | W-S |

A particular example of such an as-synthesized, swellable material is the material or Example 1 of the aforementioned U.S. Pat. No. 4,954,325. This material of example 1 of U.S. Pat. No. 4,954,325 has the X-ray diffraction pattern given in the following table II:

TABLE II

| 2 Theta | Interplanar d-Spacing (Å) | Relative Intensity, $I/I_o \times 100$ |
|---|---|---|
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |

TABLE II-continued

| 2 Theta | Interplanar d-Spacing (Å) | Relative Intensity, $I/I_o \times 100$ |
|---|---|---|
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

The as-synthesized known MCM-22 crystalline material of example 1 of U.S. Pat. No. 4,954,325 has no peak between 26.6 to 29° (2θ) in its X-ray diffraction pattern.

In its calcined form, the known MCM-22 crystalline material has an X-ray diffraction pattern which is distinguished from the patterns of other known crystalline materials by the lines listed in Table III below:

TABLE III

| Interplanar d-Spacing (Å) | Relative Intensity, $I/I_o \times 100$ |
|---|---|
| 30.0 ± 2.2 | W-M |
| 22.1 ± 1.3 | W | more specifically by the lines listed in Table IV below:

TABLE IV

| Interplanar d-Spacing (Å) | Relative Intensity, $I/I_o \times 100$ |
|---|---|
| 30.0 ± 2.2 | W-M |
| 22.1 ± 1.3 | W |
| 3.91 ± 0.07 | M-VS | and yet more specifically by the lines listed in Table V below:

TABLE V

| Interplanar d-Spacing (Å) | Relative Intensity, $I/I_o \times 100$ |
|---|---|
| 30.0 ± 2.2 | W-M |
| 22.1 ± 1.3 | W |
| 6.00 ± 0.10 | M-W |
| 4.64 ± 0.08 | W |
| 4.06 ± 0.07 | W-S |
| 3.91 ± 0.07 | M-VS |

The MCM-22 family molecular sieve composition of this invention is characterized by at least one additional peak between 26.6 to 29° (2θ) in its X-ray diffraction pattern of as-synthesized material, which is exemplified by examples 1 and 2 (FIG. 1). The calcined material is generally having substantially similar XRD pattern of calcined material as listed in tables III, IV, or V.

Scanning Electron Microscope (SEM)

The SEM images were obtained on a HITACHI S4800 Field Emission Scanning Electron Microscope (SEM).

Figure 3:
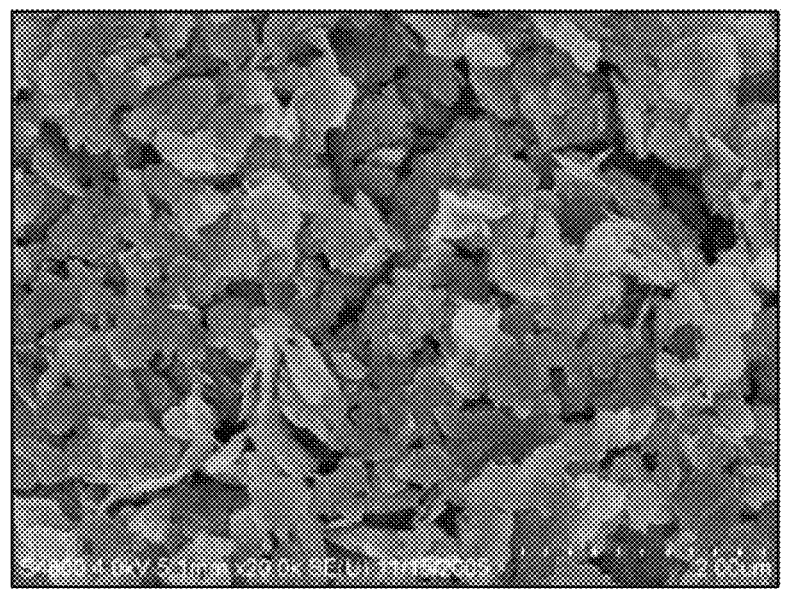
FIG. 3 shows the SEM image of the as-synthesized MCM-22 family molecular sieve product of Example 1.
Figure 4:
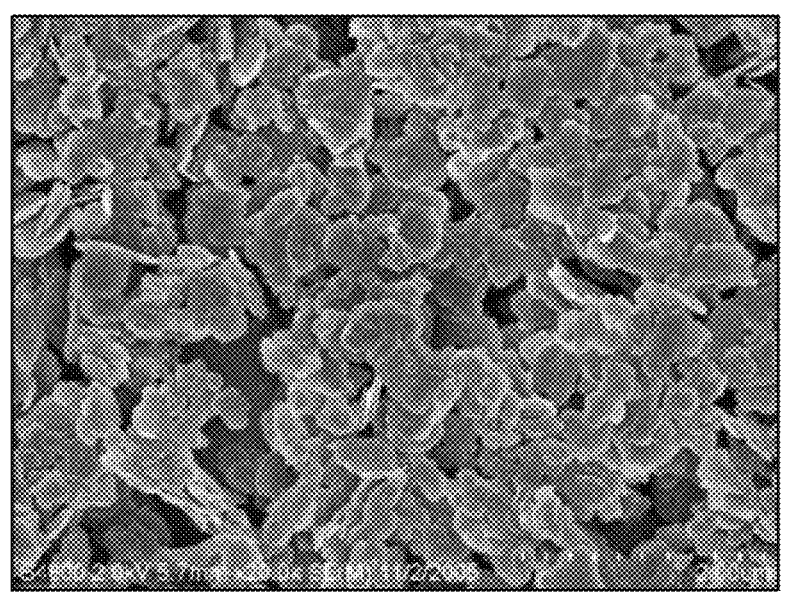
FIG. 4 shows the SEM image of the as-synthesized MCM-22 family molecular sieve product of Example 2.

The SEM image of the MCM-22 molecular sieve produced according to the method of manufacturing of U.S. Pat. No. 4,954,325 is shown in FIG. 3. The MCM-22 molecular sieve according to method of manufacturing of U.S. Pat. No. 4,954,325 has a thin layered less defined hexagonal platelets morphology and an average platelet diameter of less than about 1 µm. The SEM image of the molecular sieve of MWW framework type of this invention is shown in FIG. 4. The MCM-22 family molecular sieve of this invention (FIG. 4) has a thin layered better defined hexagonal platelets morphology than these in FIG. 3 and substantially similar average platelet diameter. However, the particles of the MCM-22 of this invention are generally thicker than the particles of the MCM-22 produced according to the method of manufacturing of U.S. Pat. No. 4,954,325.

In one embodiment of this invention, the MCM-22 family molecular sieve composition of this invention is characterized by majority, preferably at least 80 wt. %, more preferably at least 90 wt. %, of the crystal platelets having a crystal platelet thickness of at least about 300 Å, preferably at least 350 Å, more preferably at least 400 Å, even more preferably at least 450 Å, and most preferably at least 500 Å.

Surface Areas and Adsorption Uptake

Surface area of a molecular sieve may be measured by the Brunauer-Emmett-Teller (BET) method using adsorption-desorption of nitrogen (temperature of liquid nitrogen, 77 K). The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

The MCM-22 family molecular sieve composition of this invention is characterized by its low external surface area (measured by BET method) of the calcined form of the MCM-22 family molecular sieve composition. In one embodiment, the MCM-22 family molecular sieve composition of this invention is characterized by majority, preferably at least 80 wt. % of the particles having external surface area of less than 110 m²/g, optionally less than 100 m²/g or less than 90 m²/g. The surface area, including external and internal surface areas, as used in this invention, are measured based on the calcined form of the MCM-22 family molecular sieve.

The lower external surface area of the calcined MCM-22 family molecular sieve composition of this invention is consistent with the thicker platelet morphology of the MCM-22 family molecular sieve composition of this invention as exemplified in examples 1 and 2.

The adsorption uptake and sorption rate may be measured by mesitylene adsorption. The equilibrium amount of mesitylene uptake and rate of update were calculated as described in "Principles and Practice of Heterogeneous Catalysis", eds. J. M. Thomas, and W. J. Thomas, First Edition, 1997, the entirety of which is incorporated as reference. The MCM-22 family molecular sieve composition of this invention may be characterized by a mesitylene uptake of less than 29 mg/g, preferably less than 25 mg/g, measured at 0.266 kPa-a (2 torr) mesitylene partial pressure and 100° C. The MCM-22 family molecular sieve composition of this invention may also be characterized by a mesitylene sorption rate of less than 60 mg/g/min, preferably less than 50 mg/g/min, measured at 0.266 kPa-a (2 torr) mesitylene partial pressure and 100° C.

Formulation of the Hydrothermal Reaction Mixtures

Synthetic zeolites are often prepared from aqueous hydrothermal reaction mixtures (synthesis mixture(s) or synthetic gel(s)) comprising sources of appropriate oxides. Organic directing agents may also be included in the hydrothermal reaction mixture for the purpose of influencing the production of a zeolite having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

After the components of the hydrothermal reaction mixture are properly mixed with one another, the hydrothermal reaction mixture is subjected to appropriate crystallization conditions. Such conditions usually involve heating of the hydrothermal reaction mixture to an elevated temperature possibly with stirring. Room temperature aging of the hydrothermal reaction mixture is also desirable in some instances.

After the crystallization of the hydrothermal reaction mixture is complete, the crystalline product may be recovered from the remainder of the hydrothermal reaction mixture, especially the liquid contents thereof. Such recovery may involve filtering the crystals and washing these crystals with water. However, in order to remove the entire undesired residue of the hydrothermal reaction mixture from the crystals, it is often necessary to subject the crystals to a high temperature calcination e.g., at 500° C., possibly in the presence of oxygen. Such a calcination treatment not only removes water from the crystals, but this treatment also serves to decompose and/or oxidize the residue of the organic directing agent which may be occluded in the pores of the crystals, possibly occupying ion exchange sites therein.

This MCM-22 material may be prepared from a hydrothermal reaction mixture containing sources of alkali or alkaline earth metal (M) hydroxide, e.g., sodium or potassium, cation, a source of ions of trivalent element X, e.g., aluminum, a source of ions of tetravalent element Y, e.g., silicon, an organic (R) directing agent, hereinafter more particularly described, and water, said hydrothermal reaction mixture having a composition, in terms of mole ratios of oxides, within the following ranges:

TABLE VI

| Reactants | Useful | Preferred |
|---|---|---|
| $YO_2/X_2O_3$ | 10 to infinity | 15-50 |
| $H_2O/YO_2$ | 1-20 | 5-15 |
| $OH^-/YO_2$ | 0.001-2 | 0.01-0.3 |
| $M/YO_2$ | 0.001-2 | 0.01-0.3 |
| $R/YO_2$ | 0.001-0.34 | 0.01-0.34 |

The sources of the various elements required in the final product may be any of those in commercial use or described in the literature, as may the method of preparation of the synthesis mixture.

In the present synthesis method, the source of ions of tetravalent element $YO_2$ comprises solid $YO_2$, preferably about 30 wt. % solid $YO_2$ in order to obtain the crystal product of this invention. Examples of tetravalent element are silicon, germanium, and tin. When $YO_2$ is silica, the use of a silica source containing preferably about 30 wt. % solid silica, e.g., silica sold by Degussa under the trade names Aerosil or Ultrasil (a precipitated, spray dried silica containing about 90 wt. % silica), an aqueous colloidal suspension of silica, for example one sold by Grace Davison under the trade name Ludox, or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micro) favors crystal formation from the above mixture. Preferably, therefore, the $YO_2$, e.g., silica, source contains about 30 wt. % solid $YO_2$, e.g., silica, and more preferably about 40 wt. % solid $YO_2$, e.g., silica. The source of silicon may also be a silicate, e.g., an alkali metal silicate, or a tetraalkyl orthosilicate.

The source of ions of tetravalent element $X_2O_3$, e.g., aluminum, boron, gallium, and iron, is preferably aluminum sulphate or hydrated alumina. Other aluminum sources include, for example, other water-soluble aluminum salts, sodium aluminate, or an alkoxide, e.g., aluminum isopropoxide, or aluminum metal, e.g., in the form of chips.

The alkali metal is advantageously potassium or sodium, the sodium source advantageously being sodium hydroxide or sodium aluminate.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

A factor affects the cost and the product quality of the synthesis of a crystalline molecular sieve is the amount of the directing agent. The directing agent is generally the most expensive reactant(s) in the hydrothermal reaction mixture of many crystalline molecular sieves. The lower the amount of the directing agent in the hydrothermal reaction mixture, the cheaper the final molecular sieve produced. The term "low directing agent" as used herein means the molar ratio of the directing agent over the tetravalent element in the hydrothermal reaction mixture is less than 0.5, preferably less than 0.34, even more preferably less than 0.2, and most preferably less than 0.15.

In one embodiment, this invention $R:SiO_2$ molar ratio ranges from 0.001 to 0.34, preferably from 0.001 to 0.3, more preferably from 0.001 to 0.25, even more preferably from 0.001 to 0.2, and most preferably from 0.1 to 0.15.

It should be realized that the hydrothermal reaction mixture components can be supplied by more than one source. The hydrothermal reaction mixture can be prepared either batchwise or continuously. Crystal size and crystallization time of the new MCM-22 family molecular sieve will vary with the nature of the hydrothermal reaction mixture employed and the crystallization conditions.

It will be understood by a person skilled in the art that the synthesis mixture having a composition within the molar ranges as discussed above means that the synthesis mixture is the product of mixing, adding, reacting, or by any means of providing such a mixture, wherein such product has a composition within the molar ranges as discussed above. The product of mixing, adding, reacting, or by any means of providing such a mixture may or may not containing individual ingredients when the synthesis mixture was prepared. The product of mixing, adding, reacting, or by any means of providing such a mixture, may even containing reaction product of individual ingredients when the synthesis mixture was prepared by mixing, adding, reacting, or by any means of providing such a mixture.

Crystallization Conditions

Crystallization of the present MCM-22 family molecular sieve can be carried out at either static or stirred condition in a reactor vessel, such as for example, autoclaves. The total useful range of temperatures for crystallization is from about 160° C. to about 250° C. for a time sufficient for crystallization to occur at the temperature used, e.g., from about 3 hours to about 72 hours, preferably from about 10 hours to about 48 hours, and most preferably from about 10 hours to about 24 hours. Thereafter, the crystals are separated from the liquid and recovered. The procedure may include an aging period, either at room temperature or, preferably, at a moderately elevated temperature, before the hydrothermal treatment ("hydrothermal reaction") at more elevated temperature. The latter may include a period of gradual or stepwise variation in temperature.

For most of the applications, the hydrothermal reaction is carried out with any type of agitation, e.g., stirring or rotating the vessel about a horizontal axis (tumbling).

Optionally the hydrothermal reaction mixture may contain seed crystals. It is well known that seeding a molecular sieve synthesis mixture frequently has beneficial effects, for example in controlling the particle size of the product, avoiding the need for an organic template, accelerating synthesis, and improving the proportion of product that is of the intended framework type. In one embodiment of this invention, synthesis of the crystalline molecular sieve is facilitated by the presence of at least 0.01 wt. %, preferably 0.1 wt. %, more preferably 0.5 wt. %, even more preferably 1 wt. %, optionally 5 wt. %, seed crystals based on total weight of silica of the hydrothermal reaction mixture.

In one embodiment, the crystalline molecular sieve of this invention comprises at least one of MCM-22, MCM-49, MCM-56, and a mix-phase of MCM-22, MCM-49, and MCM-56.

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Catalysis and Adsorption

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

The MCM-22 family molecular sieve of this invention, when employed either as an adsorbent or as a catalyst in an organic compound conversion process should be dehydrated, at least partially. This can be done by heating to a temperature in the range of 200° C. to 595° C. in an atmosphere such as air or nitrogen, and at atmospheric, subatmospheric or superatomspheric pressures for between 30 minutes and 48 hours. Dehydration can also be performed at room temperature merely by placing the silicate in a vacuum, but a longer time is required to obtain a sufficient amount of dehydration.

When used as a catalyst, the MCM-22 family molecular sieve of this invention should be subjected to thermal treatment to remove part of all of any organic constituent. The MCM-22 family molecular sieve can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of co-crystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above MCM-22 family molecular sieve, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of said catalytic reactions.

The crystals prepared by the instant invention can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The MCM-22 family molecular sieve of this invention may be used as an adsorbent, such as for separating at least one component from a mixture of components in the vapor or liquid phase having differential sorption characteristics with respect to the MCM-22 family molecular sieve of this invention. Therefore, at least one component can be partially or substantially totally separated from a mixture of components having differential sorption characteristics with respect to the MCM-22 family molecular sieve of this invention by contacting the mixture with the MCM-22 family molecular sieve of this invention to selectively sorb the one component.

The MCM-22 family molecular sieves of this invention are useful as catalyst in a wide range of processes, including separation processes and hydrocarbon conversion processes. Specific examples of hydrocarbon conversion processes which are effectively catalyzed by the MCM-22 family molecular sieve of this invention, by itself or in combination with one or more other catalytically active substances including other crystalline catalysts, include the following:

(i) alkylation of aromatic hydrocarbons, e.g., benzene, with long chain olefins, e.g., $C_{14}$ olefin, with reaction conditions including a temperature of from about 340° C. to about 500° C., a pressure of from about 101 to about 20200 kPa-a, a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and dialkylates with reaction conditions including a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including a temperature of from about 160° C. to about 260° C. and a pressure of from about 2600 to 3500 kPa-a;

(v) alkylation of phenols with olefins or equivalent alcohols to provide long chain alkyl phenols with reaction conditions including a temperature of from about 200° C. to about 250° C., a pressure of from about 1500 to 2300 kPa-a and a total WHSV of from about 2 $hr^{-1}$ to about 10 $hr^{-1}$;

(vi) conversion of light paraffins to olefins and aromatics with reaction conditions including a temperature of from about 425° C. to about 760° C. and a pressure of from about 170 to about 15000 kPa-a;

(vii) conversion of light olefins to gasoline, distillate and lube range hydrocarbons with reaction conditions including a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this invention in combination with a Group VIII metal as catalyst with effluent therefrom being reaction in a second stage using zeolite Beta, also in combination with a Group VIII metal, as catalyst, the reaction conditions including a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 $hr^{-1}$;

(ix) a combination hydrocracking/dewaxing process in the presence of the MCM-22 family molecular sieve of this invention and a hydrogenation component as catalyst, or a mixture of such catalyst and zeolite Beta, with reaction conditions including a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including a temperature of from about 20° C. to about 200° C., a pressure of from 200 to about 20000 kPa-a, a WHSV (gram-olefin per hour gram-zeolite) of from about 0.1 $hr^{-1}$ to about 200 $hr^{-1}$ and an alcohol to olefin molar feed ratio of from about 0.1/1 to about 5/1;

(xi) toluene disproportionations with $C_9$+ aromatics as co-feed with reaction conditions including a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 $h^{-1}$ to about 30 $hr^{-1}$;

(xii) preparation of the pharmaceutically-active compound 2-(4-isobutylphenyl)propionic acid, i.e. ibuprofen, by reacting isobutylbenzene with propylene oxide to provide the intermediate 2-(4-isobutylphenyl)propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene; and (xvi) in a process for decreasing the durene content of a 90-200° C.+ bottoms fraction obtained from the catalytic conversion of methanol to gasoline which comprises contacting said durene-containing bottoms fraction with hydrogen over a catalyst of the present MCM-22 family molecular sieve with a hydrogenation metal, at conditions including a temperature of from about 230° C. to about 425° C. and a pressure of from about 457 to about 22000 kPa-a.

In an embodiment, the MCM-22 family molecular sieves of this invention may be used in processes that co-produce phenol and ketones that proceed through benzene alkylation, followed by formation of the alkylbenzene hydroperoxide and cleavage of the alkylbenzene hydroperoxide into phenol and ketone. In such processes, the MCM-22 family molecular sieves of this invention are used in the first step, that is, benzene alkylation. Examples of such processes includes processes in which benzene and propylene are converted to phenol and acetone, benzene and C4 olefins are converted to phenol and methyl ethyl ketone, such as those described for example in international application PCT/EP2005/008557, benzene, propylene and C4 olefins are converted to phenol, acetone and methyl ethyl ketone, which, in this case can be followed by conversion of phenol and acetone to bis-phenol-A as described in international application PCT/EP2005/008554, benzene is converted to phenol and cyclohexanone, or benzene and ethylene are converted to phenol and methyl ethyl ketone, as described for example in PCT/EP2005/008551.

The MCM-22 family molecular sieves of this invention are useful in benzene alkylation reactions where selectivity to the monoalkylbenzene is required. Furthermore, the MCM-22 family molecular sieves of this invention is particularly useful to produce selectively sec-butylbenzene from benzene and C4 olefin feeds that are rich in linear butenes, as described in international application PCT/EP2005/008557. Preferably, this conversion is carried out by co-feeding benzene and the C4 olefin feed with the catalyst of the present invention, at a temperature of about 60° C. to about 260° C., for example of about 100° C. to 200° C., a pressure of 7000 kPa-a or less, and a feed weight hourly space velocity (WHSV) based on C4 alkylating agent of from about 0.1 to 50 hr$^{-1}$ and a molar ratio of benzene to C4 alkylating agent from about 1 to about 50.

The MCM-22 family molecular sieves of this invention are also useful catalyst for transalkylations, such as, for example, polyalkylbenzene transalkylations.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided MCM-22 family molecular sieve and inorganic oxide matrix vary widely, with the crystal content ranging from about 1 to about 90 percent by weight and more usually, particularly when the composite is prepared in the form of beads, in the range of about 2 to about 80 wt. % of the composite.

In one embodiment, this invention relates to:
1. an MCM-22 family molecular sieve which has a platelet morphology having a crystal thickness at least 300 Å measured by SEM;
2. the MCM-22 family molecular sieve of paragraph 1, having an external surface area is less than 110 m$^2$/g measured by BET;
3. the MCM-22 family molecular sieve of paragraphs 1-2, having an X-ray diffraction pattern of as-synthesized said MCM-22 family molecular sieve including d-spacing maxima at 12.4±0.25, 3.57±0.07 and 3.42±0.07 Angstroms and at least one peak between 26.6° and 29° (2θ);
4. the MCM-22 family molecular sieve of paragraph 3, wherein said peak between 26.6° to 29° (2θ) has a two theta (2θ) of about 26.9°;
5. the MCM-22 family molecular sieve of paragraphs 1-4, having a mesitylene uptake of less than 29 mg/g measured at 0.266 kPa-a (2 torr) mesitylene partial pressure and 100° C.;
6. the MCM-22 family molecular sieve of paragraphs 1-5, having an X-ray diffraction pattern of calcined said MCM-22 family molecular sieve includes values substantially as shown in Table III;
7. the MCM-22 family molecular sieve to paragraphs 1-6, having an X-ray diffraction pattern of calcined said MCM-22 family molecular sieve includes values substantially as shown in Table IV;
8. the MCM-22 family molecular sieve to paragraphs 1-7, having an X-ray diffraction pattern of calcined said MCM-22 family molecular sieve includes values substantially as shown in Table V;
9. an MCM-22 family molecular sieve having an external surface area less than 110 m$^2$/g measured by BET;
10. the MCM-22 family molecular sieve of paragraph 9, wherein said external surface area is less than 100 m$^2$/g;
11. the MCM-22 family molecular sieve of paragraphs 2-10, wherein said external surface area is less than 90 m$^2$/g;
12. the MCM-22 family molecular sieve of paragraphs 2-11, wherein said external surface area is less than 85 m$^2$/g;
13. the MCM-22 family molecular sieve of paragraphs 9-12, having a platelet morphology having a crystal thickness at least 300 Å measured by SEM;
14. the MCM-22 family molecular sieve of paragraphs 9-13, having an X-ray diffraction pattern of as-synthesized said MCM-22 family molecular sieve including d-spacing maxima at 12.4±0.25, 3.57±0.07 and 3.42±0.07 Angstroms and at least one peak between 26.6° and 29° (2θ);
15. the MCM-22 family molecular sieve of paragraph 14, wherein said peak between 26.6° to 29° (2θ) has a two theta (2θ) of about 26.9°;
16. the MCM-22 family molecular sieve of paragraphs 9-15, having an X-ray diffraction pattern of calcined said MCM-22 family molecular sieve includes values substantially as shown in Table III;
17. the MCM-22 family molecular sieve to paragraphs 9-16, having an X-ray diffraction pattern of calcined said MCM-22 family molecular sieve includes values substantially as shown in Table IV;
18. the MCM-22 family molecular sieve to paragraphs 9-17, having an X-ray diffraction pattern of calcined said MCM-22 family molecular sieve includes values substantially as shown in Table V;
19. an MCM-22 family molecular sieve having a mesitylene uptake of less than 29 mg/g measured at 0.266 kPa-a (2 torr) mesitylene partial pressure and 100° C.;
20. the MCM-22 family molecular sieve of paragraph 19, wherein said mesitylene uptake is less than 25 mg/g;
21. the MCM-22 family molecular sieve of paragraphs 19-20, having a platelet morphology having a thickness at least 300 Å measured by SEM;

22. the MCM-22 family molecular sieve of paragraphs 19-21, having an X-ray diffraction pattern of the as-synthesized MCM-22 family molecular sieve including d-spacing maxima at 12.4±0.25, 3.57±0.07 and 3.42±0.07 Angstroms and at least one peak between 26.6° and 29° (2θ);
23. the MCM-22 family molecular sieve of paragraph 22, wherein said peak between 26.6° to 29° (2θ) has a two theta (2θ) of about 26.9°;
24. the MCM-22 family molecular sieve of paragraphs 19-23, having an X-ray diffraction pattern of calcined said MCM-22 family molecular sieve includes values substantially as shown in Table III;
25. the MCM-22 family molecular sieve to paragraphs 19-24, having an X-ray diffraction pattern of calcined said MCM-22 family molecular sieve includes values substantially as shown in Table IV;
26. the MCM-22 family molecular sieve to paragraphs 19-25, having an X-ray diffraction pattern of calcined said MCM-22 family molecular sieve includes values substantially as shown in Table V;
27. a method of manufacturing an MCM-22 family molecular sieve of paragraphs 1-26, said method comprising the steps of:
   a. combining at least one silicon source, at least one source of alkali metal hydroxide, at least one directing-agent (R), water, and optionally one aluminum source to form a mixture having the following mole composition:
   Si:Al$_2$=10 to infinity
   H$_2$O:Si=1 to 20
   OH$^-$:Si=0.001 to 2
   M$^+$:Si=0.001 to 2
   R:Si=0.001 to 0.34
   wherein M is an alkali metal;
   b. treating said mixture at crystallization conditions for less than 72 hr to form a product having said MCM-22 family molecular sieve, wherein said crystallization conditions comprises a temperature range from about 160° C. to about 250° C.; and
   c. recovering said molecular sieve;
28. a process for hydrocarbon conversion, said process comprising the steps of:
   a. contacting a hydrocarbon feedstock with an MCM-22 family molecular sieve recited in paragraphs 1-26 under conversion conditions to form a product; and
   b. withdrawing said product.

These and other facets of the present invention is exemplified from the examples followed.

EXAMPLES

The following examples illustrate exemplary preferred embodiments:

In these examples, the XRD diffraction patterns of the as-synthesized materials were recorded on an X-Ray Powder Diffractometer using copper Kα radiation in the 2θ range of 2 to 40 degrees.

The Scanning Electron Microscope (SEM) images were obtained on a HITACHI S4800 Field Emission Scanning Electron Microscope.

The crystallinity is defined as the ratio of the sum of the two main peaks, 7.1 and 26 (2θ), to the ratio of the sum of the same peaks in the standard (reference example), multiplied by 100.

The total surface area was measured by the BET method. The micropore surface area was determined by the t-plot method. The BET surface area measurements were carried out using a commercial unit of Micromeritics TriStar 3000 (Micromeritics Corporation, Norcross, Ga.).

The mesitylene uptake and sorption rate was measured placing a weighted sample of the calcined molecular sieve in contacting with vapor mesitylene at a mesitylene partial pressure of 0.2666 kPa-a (2 torr) at 100° C. The partial pressure was kept constant by continuously flowing vapor mesitylene to the adsorption chamber. The increase of weight was measured with time on stream. The equilibrium amount of mesitylene uptake and rate of update were calculated as described in "Principles and Practice of Heterogeneous Catalysis", eds. J. M. Thomas, and W. J. Thomas, First Edition, 1997.

Example 1

Comparative Example

A hydrothermal reaction mixture was prepared from water, Hexamethyleneimine (HMI) (Sigma-Aldrich Company), Ultrasil™ (Degussa Corp.), 45 wt. % sodium aluminate solution, and 50 wt. % sodium hydroxide solution. The mixture had the following molar composition:

| | Example 1 (Reference Example) |
|---|---|
| Hydrothermal Reaction Mixture Molar Composition | |
| SiO$_2$/Al$_2$O$_3$ | ~30 |
| H$_2$O/SiO2 | ~19.8 |
| OH$^-$/SiO$_2$ | ~0.17 |
| Na$^+$/SiO$_2$ | ~0.17 |
| HMI/SiO$_2$ | ~0.35 |
| Crystallization Conditions | |
| Temperature (° C.) | 150 |
| Stirring speed (RPM) | 250 |
| Time (hr) | 72 |
| Product Characterization | |
| XRD Result | Pure Phase MCM-22 |
| Crystallinity (%) | 100 |
| SiO$_2$/Al$_2$O$_3$ (molar ratio) | ~23 |
| Total Surface Area (m$^2$/g) | 653 |
| Micropore Surface Area (m$^2$/g) | 530 |
| External Surface Area (m$^2$/g) | 123 |
| Mesitylene uptake (mg/g) | 29.8 |
| Mesitylene sorption rate (mg/g/min) | 68 |

Figure 2:
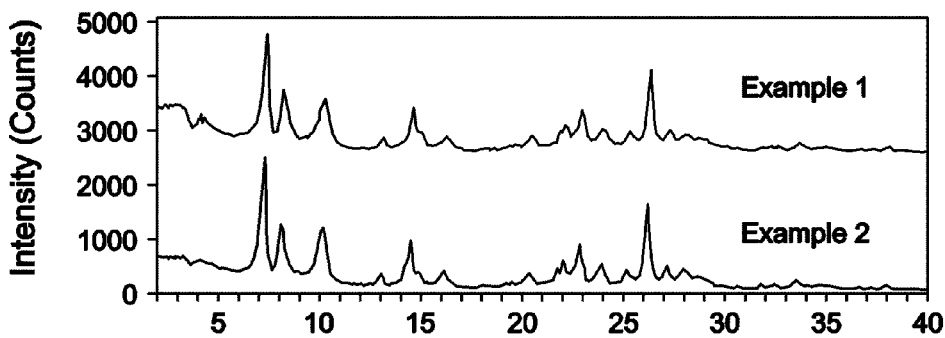
FIG. 2 shows X-ray diffraction patterns of the calcined MCM-22 family molecular sieve products of Examples 1 and 2.

The mixture was crystallized at 150° C. in an autoclave with stirring at 250 rotation per minute (RPM) for 72 hours. After crystallization, the hydrothermal reaction mixture slurry was filtered, washed with deionized (DI) water and dried at 120° C. The XRD patterns of the calcined material (FIG. 2) showed the typical pure phase of MCM-22 topology substantially as Tables III, IV, and V. The as-synthesized material had an XRD patterns (FIG. 1) substantially as shown in Table I and Table II and only one peak (about) 26.5° between 26° to 29° (2θ). The resulting MCM-22 crystals had a SiO$_2$/Al$_2$O$_3$ molar ratio of ~23/1. The calcined MCM-22 crystals had a surface area of 653 m$^2$/g (micropore surface area of 530 and external surface area of 123 m$^2$/g). The SEM image (FIG. 3) of the as-synthesized product crystal showed a platelet morphology with an average crystal thickness of about 200 to about 300 Å. The estimate average platelet diameter was less than about 1 μm. The calcined material had a mesitylene uptake of about 29.8 mg/g and a mesitylene sorption rate of about 68 mg/g/min.

Example 2

A hydrothermal reaction mixture were prepared from water, Hexamethyleneimine (HMI) (Sigma-Aldrich Company), Ultrasil™ (Degussa Corp.), 45 wt. % sodium aluminate solution, and 50 wt. % sodium hydroxide solution. The mixtures had the following molar compositions:

|  | Example 2 |
|---|---|
| Hydrothermal Reaction Mixture Molar Composition | |
| $SiO_2/Al_2O_3$ | ~30 |
| $H_2O/SiO2$ | ~13 |
| $OH^-/SiO_2$ | ~0.15 |
| $Na^+/SiO_2$ | ~0.15 |
| $HMI/SiO_2$ | ~0.2 |
| Crystallization Conditions | |
| Temperature (° C.) | 170 |
| Stirring speed (RPM) | 250 |
| Time (hr) | 24 |
| Product Characterization | |
| XRD Result | Pure Phase MCM-22 |
| Crystallinity (%) | 105 |
| $SiO_2/Al_2O_3$ (molar ratio) | ~24 |
| Total Surface Area (m$^2$/g) | 612 |
| Micropore Surface Area (m$^2$/g) | 528 |
| External Surface Area (m$^2$/g) | 84 |
| Mesitylene uptake (mg/g) | 24.7 |
| Mesitylene sorption rate (mg/g/min) | 45 |

The mixture of example 2 was crystallized at 170° C. in an autoclave with stirring at 250 rotation per minute (RPM) for 24 hours. After crystallization, the hydrothermal reaction mixture slurry of example 2 was filtered, washed with deionized (DI) water and dried at 120° C. The XRD patterns of the calcined material (FIG. 2) showed the typical pure phase of MCM-22 topology substantially as shown in Tables III, IV, and V. The as-synthesized material had an XRD patterns (FIG. 1) substantially as shown in Table I and Table II and an additional peak (26.9°) between 26.6° to 29° (2θ) as comparing to the example 1 (reference example). The resulting MCM-22 crystals had crystallinity of 105%, which is measured by the ratio of the sum of the two main peaks (2θ at 7.1 and 26) to the ratio of the sum of the same peaks in the example 1 (reference example). The resulting MCM-22 crystals had a $SiO_2/Al_2O_3$ molar ratio of ~24/1. The calcined MCM-22 crystals had a surface area of 612 m$^2$/g (micropore surface area of 528 and external surface area of 84 m$^2$/g). The SEM image (FIG. 4) of the as-synthesized product crystal showed a platelet morphology with an average crystal thickness of at least 300 Å, which is thicker than the reference example. The estimate average crystal thickness measured by SEM was about 300 Å to about 500 Å. The estimate average platelet diameter was less than about 1 μm, which is similar as the reference example. The calcined material had a mesitylene uptake of about 24.7 mg/g and a mesitylene sorption rate of about 45 mg/g/min.

The results showed that:
(i) the MCM-22 crystal of example 2 had similar average platelet diameter (estimate less than about 1 μm based on SEM) as the MCM-22 crystal of example 1;
(ii) the MCM-22 crystal of example 2 had lower external surface area than the external surface area of the MCM-22 crystal of example 1, wherein the MCM-22 crystal of example 2 was made with higher temperature and shorter crystallization time than these of the MCM-22 crystal of example 1;
(iii) the as-synthesized MCM-22 crystal of example 2 had an additional XRD peak (26.9°) between 26.6° to 29° (2θ) comparing to the as-synthesized MCM-22 crystal of example 1 having no resolved XRD peak between 26.6° to 29° (2θ);
(iv) the MCM-22 crystal of example 2 had higher crystallinity than the crystallinity of the MCM-22 crystal of example 1;
(v) the MCM-22 crystal of example 2 had a crystal platelet thickness which is thicker than the crystal platelet thickness of the MCM-22 crystal of example 1; and/or
(vi) the MCM-22 crystal of example 2 had lower mesitylene update and mesitylene sorption rate than the MCM-22 crystal of example 1.

We concluded that we had discovered a new composition of matter having a MWW framework type, which is characterized by at least one additional XRD peak (26.9°) between 26.6° to 29° (2θ) of the as-synthesized material. The new composition of matter may also be characterized by at least 80 wt. % of the crystal platelet having an average crystal thickness of at least about 300 Å that is thicker than the reference example. The new composition of matter may also be characterized by lower external surface area than that of the reference example. The new composition of matter may also be characterized by lower mesitylene uptake and sorption rate than these of the reference example.

While the illustrative embodiments of this invention have been described with particularity, it will be understood that various other modifications will be apparent to and can be readily made by those skilled in the art without departing from the spirit and scope of this invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. An MCM-22 family molecular sieve having an X-ray diffraction pattern of as-synthesized said MCM-22 family molecular sieve including d-spacing maxima at 12.4±0.25, 3.57±0.07 and 3.42±0.07 Angstroms and at least one peak between 26.6° and 29° (2θ).

2. The MCM-22 family molecular sieve to claim 1 having a peak between 26.6° and 29° (2θ) with a two theta (2θ) value of about 26.9°.

3. The MCM-22 family molecular sieve to claim 1, wherein the X-ray diffraction pattern includes values substantially as shown in Table I.

4. The MCM-22 family molecular sieve of claim 1, having a platelet morphology having a crystal thickness at least 300 Å measured by SEM.

5. The MCM-22 family molecular sieve of claim 1 having an external surface area less than 110 m$^2$/g measured by BET.

6. The MCM-22 family molecular sieve of claim 1 having a mesitylene uptake of less than 29 mg/g measured at 0.266 kPa-a (2 torr) mesitylene partial pressure and 100° C.

7. The MCM-22 family molecular sieve of claim 1, having an X-ray diffraction pattern of calcined said MCM-22 family molecular sieve includes values substantially as shown in Table III.

8. The MCM-22 family molecular sieve to claim 1, having an X-ray diffraction pattern of calcined said MCM-22 family molecular sieve includes values substantially as shown in Table IV.

9. The MCM-22 family molecular sieve to claim 1, having an X-ray diffraction pattern of calcined said MCM-22 family molecular sieve includes values substantially as shown in Table V.

10. An MCM-22 family molecular sieve which has a platelet morphology having a crystal thickness at least 300 Å measured by SEM.

11. The MCM-22 family molecular sieve of claim 10, having an external surface area is less than 110 m²/g measured by BET.

12. The MCM-22 family molecular sieve of claim 10, having an X-ray diffraction pattern of as-synthesized said MCM-22 family molecular sieve including d-spacing maxima at 12.4±0.25, 3.57±0.07 and 3.42±0.07 Angstroms and at least one peak between 26.6° and 29° (2θ), wherein said peak between 26.6° to 29° (2θ) has a two theta (2θ) of about 26.9°.

13. The MCM-22 family molecular sieve of claim 10, having a mesitylene uptake of less than 29 mg/g measured at 0.266 kPa-a (2 torr) mesitylene partial pressure and 100° C.

14. The MCM-22 family molecular sieve of claim 10, having an X-ray diffraction pattern of calcined said MCM-22 family molecular sieve includes values substantially as shown in Table III.

15. The MCM-22 family molecular sieve to claim 10, having an X-ray diffraction pattern of calcined said MCM-22 family molecular sieve includes values substantially as shown in Table IV.

16. The MCM-22 family molecular sieve to claim 10, having an X-ray diffraction pattern of calcined said MCM-22 family molecular sieve includes values substantially as shown in Table V.

17. An MCM-22 family molecular sieve having an external surface area less than 110 m²/g measured by BET, having a platelet morphology and a crystal thickness of at least 300 Å measured by SEM, and having an X-ray diffraction pattern of as-synthesized said MCM-22 family molecular sieve including d-spacing maxima at 12.4±0.25, 3.57±0.07 and 3.42±0.07 Angstroms and at least one peak between 26.6° and 29° (2θ).

18. The MCM-22 family molecular sieve of claim 17, wherein said peak between 26.6° to 29° (2θ) has a two theta (2θ) of about 26.9°.

19. The MCM-22 family molecular sieve of claim 17, having an X-ray diffraction pattern of calcined said MCM-22 family molecular sieve includes values substantially as shown in Table III.

20. The MCM-22 family molecular sieve to claim 17, having an X-ray diffraction pattern of calcined said MCM-22 family molecular sieve includes values substantially as shown in Table IV.

21. An MCM-22 family molecular sieve having a mesitylene uptake of less than 29 mg/g measured at 0.266 kPa-a (2 torr) mesitylene partial pressure and 100° C.

22. The MCM-22 family molecular sieve of claim 21, having a platelet morphology having a thickness of at least 300 Å measured by SEM, and having an X-ray diffraction pattern of the as-synthesized MCM-22 family molecular sieve including d-spacing maxima at 12.4±0.25, 3.57±0.07 and 3.42±0.07 Angstroms and at least one peak between 26.6° and 29° (2θ).

23. The MCM-22 family molecular sieve of claim 22, wherein said peak between 26.6° to 29° (2θ) has a two theta (2θ) of about 26.9°.

24. The MCM-22 family molecular sieve of claim 21, having an X-ray diffraction pattern of calcined said MCM-22 family molecular sieve includes values substantially as shown in Table III.

25. A method of manufacturing an MCM-22 family molecular sieve, said method comprising the steps of:
- (a) combining at least one silicon source, at least one source of alkali metal hydroxide, at least one directing-agent (R), water, and optionally one aluminum source to form a mixture having the following mole composition:
  Si:Al$_2$=10 to infinity
  H$_2$O:Si=1 to 20
  OH$^-$:Si=0.001 to 2
  M$^+$:Si=0.001 to 2
  R:Si=0.001 to 0.34
  wherein M is an alkali metal;
- (b) treating said mixture at crystallization conditions for less than 72 hr to form a product having said MCM-22 family molecular sieve, wherein said crystallization conditions comprises a temperature range from about 160° C. to about 250° C.; and
- (c) recovering said molecular sieve.

* * * * *